United States Patent [19]
Ao et al.

[11] Patent Number: 5,710,299
[45] Date of Patent: Jan. 20, 1998

[54] PRODUCTION OF BRIDGED METALLOCENE COMPLEXES AND INTERMEDIATES THEREFOR

[75] Inventors: Meng-Sheng Ao; Hassan Y. Elnagar; Arcelio J. Malcolm; Jamie R. Strickler, all of Baton Rouge, La.

[73] Assignee: Albemarle Corporation, Richmond, Va.

[21] Appl. No.: 672,128

[22] Filed: Jun. 27, 1996

[51] Int. Cl.$^6$ .................................................. C07F 17/00
[52] U.S. Cl. ........................... 556/53; 556/43; 556/58; 556/95; 556/478; 568/808; 585/357; 502/103; 502/117; 526/160; 526/943
[58] Field of Search .................. 585/357; 568/808, 568/807; 556/478, 95, 58, 53, 43

[56] References Cited

U.S. PATENT DOCUMENTS

| | | | |
|---|---|---|---|
| 4,528,408 | 7/1985 | Plummer | 568/808 |
| 4,794,096 | 12/1988 | Ewen | 502/117 |
| 4,892,851 | 1/1990 | Ewen et al. | 502/104 |
| 4,931,417 | 6/1990 | Miya et al. | 502/117 |
| 5,017,714 | 5/1991 | Welborn, Jr. | 556/12 |
| 5,036,034 | 7/1991 | Ewen | 502/117 |
| 5,120,867 | 6/1992 | Welborn, Jr. | 556/12 |
| 5,145,819 | 9/1992 | Winter et al. | 502/117 |
| 5,296,434 | 3/1994 | Karl et al. | 502/117 |
| 5,314,973 | 5/1994 | Welborn, Jr. | 526/126 |
| 5,324,800 | 6/1994 | Welborn, Jr. et al. | 526/160 |
| 5,329,033 | 7/1994 | Spaleck et al. | 556/53 |
| 5,441,920 | 8/1995 | Welborn, Jr. | 502/103 |
| 5,455,365 | 10/1995 | Winter et al. | 556/7 |
| 5,455,366 | 10/1995 | Rohrmann et al. | 556/8 |
| 5,512,693 | 4/1996 | Rosen et al. | 556/7 |
| 5,532,396 | 7/1996 | Winter et al. | 556/11 |
| 5,541,350 | 7/1996 | Murata et al. | 556/10 |
| 5,556,997 | 9/1996 | Strickler et al. | 556/11 |
| 5,569,746 | 10/1996 | Lee et al. | 534/11 |
| 5,585,508 | 12/1996 | Kuber et al. | 556/11 |

FOREIGN PATENT DOCUMENTS

| | | |
|---|---|---|
| 2055218 | 5/1992 | Canada . |
| 2084016 | 5/1993 | Canada . |
| 2084017 | 5/1993 | Canada . |
| 0549900 | 11/1992 | European Pat. Off. . |
| 0530908 | 3/1993 | European Pat. Off. . |
| 0581754 | 2/1994 | European Pat. Off. . |
| 0659757 | 12/1994 | European Pat. Off. . |
| 4434640 | 2/1996 | Germany . |
| 646438 | 11/1984 | Switzerland . |

OTHER PUBLICATIONS

Stehling et al., Ansa–Zirconocene Polymerization Catalysts with Annelated Ring Ligands—Effects on Catalytic Activity and Polymer Chain Length, Organometallics, 1994, vol. 13, No. 3, pp. 964–970.

Ray and Westland; "The Infrared Spectra of Some Compounds of Zirconium(IV) and Hafnium(IV) Tetrahalides and Ligands Containing Group V Donor Atoms"; Inorganic Chemistry, vol. 4, No. 10, Oct. 1965, pp. 1501–1504.

Spaleck, et al., The Influence of Aromatic Substituents on the Polymerization Behavior of Bridged Zirconocene Catalysts; Organometallics, vol. 13, No. 3, 1994, pp. 954–963.

Spaleck, et al., "High Molecular Weight Polypropylene through Specifically Designed Zirconocene Catalysts"; Angew Chem. Int. Ed. Engl, 1992, vol. 31, No. 10, pp. 1347–1350.

Jordan, et al., "Synthesis and Structures of Neutral and Cationic rac–(Ethylenebis(tetrahydroindenyl))zirconium (IV) Benzyl Complexes"; Organometallics, vol. 9, No. 5, 1990, pp. 1539–1545.

Samuel et al; "π–Cyclopentadienyl and π–Indenyl Compounds of Titanium, Zirconium, and Hafnium Containing σ–Bonded Organic Substituents"; Journal of the American Chemical Society, 1973, 95:19; pp. 6263–6267.

The Metallocene Monitor, Special Feature; Hoechst, and BASF All Have Parts of Metallocene–Catalyzed Isotactic PP; pp. 4–10; (undated).

Stehling, et al., "ansa–Zirconocene Polymerization Catalysts with Annelated Ring Ligands–Effects on Catalytic Activity and Polymer Chain Length"; Organometallics, 1994, vol. 13, No. 3, pp. 964–970.

Morrison and Boyd 3rd Edition "Organic Chemistry" pp. 630, 636.

*Primary Examiner*—Porfirio Nazario-Gonzalez
*Assistant Examiner*—Jean F. Vollano
*Attorney, Agent, or Firm*—Philip M. Pippenger

[57] ABSTRACT

Bridged metallocene compounds are produced by a process of promising commercial utility for plant-sized operations. The overall process involves the direct conversion of benzoindanones to benzoindanols which, without isolation, are converted to benzoindenes. Thereupon the benzoindenes are bridged by deprotonating the benzoindenes with a strong base such as butyllithium and reacting the resultant deprotonated product with a suitable silicon-, germanium- or tin-containing bridging reactant such as dichlorodimethylsilane. The resultant bridged product is deprotonated with a strong base such as butyllithium and reacted with a suitable Group IV, V, or VI metal-containing reactant such as $ZrCl_4$ to provide a silicon-, germanium- or tin-bridged Group IV, V, or VI metal complex, such as a dihydrocarbylsilyl-bridged zirconocene complex. The initial benzoindenones used in such sequence can be formed readily and in high yield by reaction of a 2-haloacyl halide with naphthalenes unsubstituted in at least the 1- and 2-positions.

41 Claims, No Drawings

PRODUCTION OF BRIDGED METALLOCENE COMPLEXES AND INTERMEDIATES THEREFOR

TECHNICAL FIELD

This invention relates to a new, efficacious process for producing bridged metallocene complexes, such as for example dihydrocarbylsilyl-bridged zirconocene complexes, and for producing key intermediates used in the overall synthesis process.

BACKGROUND

The synthesis of certain dihydrocarbylsilyl-bridged zirconocene complexes and their use as polymerization catalyst components have been reported heretofore. See for example U. Stehling et al., *Organometallics* 1994, 13, 964–970. Rohrmann et al. U.S. Pat. No. 5,455,366 issued Oct. 3, 1995, describes multistep processes for producing a variety of metallocenes having benzo-fused indenyl derivatives as ligands. These materials are also shown to have utility in the formulation of polymerization catalysts.

While workable, these prior processes are deemed best suited for laboratory-scale operations. Thus a need exists for a simplified process which can be used to make desired bridged metallocenes, such as dihydrocarbylsilyl-bridged zirconocene complexes, in acceptable yields in large scale production facilities.

THE INVENTION

This invention provides a new process for producing bridged metallocene compounds—such as are described in the foregoing Rohrmann et al. patent—which is both efficacious and of promising commercial utility in plant-sized operations.

Unlike the Rohrmann et al. procedures, the processes of this invention involve the direct conversion of benzoindanones to benzoindanols which, without isolation, in turn are converted to benzoindenes. Thereupon the benzoindenes are bridged by deprotonating the benzoindenes with a strong base such as butyllithium and reacting the resultant deprotonated product with a suitable silicon-, germanium- or tin-containing bridging reactant. The resultant bridged product so formed is then deprotonated with a strong base such as butyllithium and reacted with a suitable Group IV, V, or VI (formerly known as Groups IVb, Vb and VIb) metal-containing reactant to provide a silicon-, germanium- or tin-bridged Group IV, V, or VI metal complex, such as a dihydrocarbylsilyl-bridged zirconocene complex. The invention thus provides, inter alia, a straightforward commercially feasible sequence of operations. Moreover, the initial benzoindenones used in the practice of such sequence can be formed readily and in high yield by reaction of a 2-haloacyl halide with naphthalenes unsubstituted in at least the 1- and 2-positions. This reaction normally produces a mixture of two isomers, namely a 4,5-benzoindan-1-one as the major isomer and a 4,5-benzoindan-3-one as the minor isomer. These isomers can, if desired, be separated from each other by known procedures. Thus unless expressly stated otherwise, the term 4,5-benzoindanone as used herein refers to at least one 4,5-benzoindan-1-one or at least one 4,5-benzoindan-3-one, or a mixture of at least one 4,5-benzoindan-1-one and at least one 4,5-benzoindan-3-one. Similarly depending on the isomeric makeup of the initial 4,5-benzoindanone(s), the conversion of a 4,5-benzoindanone to a 4,5-benzoindanol can form one or more 4,5-benzoindan-1-ols or one or more 4,5-benzoindan-3-ols, or a mixture of one or more 4,5-benzoindan-1-ols and one or more 4,5-benzoindan-3-ols. Thus unless expressly stated otherwise, the term 4,5-benzoindanol as used herein refers to at least one 4,5-benzoindan-1-ol or at least one 4,5-benzoindan-3-ol, or a mixture of at least one 4,5-benzoindan-1-ol and at least one 4,5-benzoindan-3-ol.

Thus in one of its embodiments this invention provides a process of forming a 4,5-benzoindanol which comprises mixing together at least one of each of the following: (a) a 4,5-benzoindanone, (b) an alkali or alkaline earth metal borohydride or alkali or alkaline earth metal aluminum hydride, and (c) a hydroxyl-containing compound capable of interacting with (b) to serve as a hydrogen source, such that a 4,5-benzoindanol is formed. Such borohydride or aluminum hydride reductions of the carbonyl group can be conducted with high selectivity and in good yields. The operation is preferably conducted in a liquid ether reaction medium such as tetrahydrofuran and alkyltetrahydrofurans.

The preferred 4,5-benzoindanones for use in the process are 4,5-benzoindan-1-ones or mixtures of a major molar proportion of one or more 4,5-benzoindan-1-ones and a minor molar proportion of one or more 4,5-benzoindan-3-ones, such as for example a mixture of about 90 mol % of a 4,5-benzoindan-1-one and about 10 mol % of a 4,5-benzoindan-3-one.

Sodium borohydride is the preferred reducing agent, but use can be made of other compounds such as sodium aluminum tetrahydride, sodium aluminum hexahydride, and their lithium or potassium analogs. Generally speaking, the alkali metal derivatives are preferred over the alkaline earth compounds, and as compared to the hexahydrides, the tetrahydrides are the more preferred reagents, especially the borohydrides. Such more preferred reagents may thus be depicted by the formula $AMH_x(OR)_y$ wherein A is an alkali metal, M is boron or aluminum, R is hydrocarbyl, x is an integer in the range of 2 to 4, and y is an integer in the range of 0 to 2, the sum of x and y being 4. Most preferably y is zero and M is boron.

The hydroxyl-containing component used in the reaction as a source of hydrogen is either water or a suitable hydroxyorganic compound such as an alcohol, a polyol, or a phenol. Water or lower alkanols or mixtures thereof are preferred.

The 4,5-benzoindanones used in this reaction are illustrated by formula (A) below which for convenience depicts the 4,5-benzoindan-1-ones. The 4,5-benzoindan-3-ones have the same formula except that the keto functionality is in the 3-position of the 5-membered ring instead of the 1-position as shown.

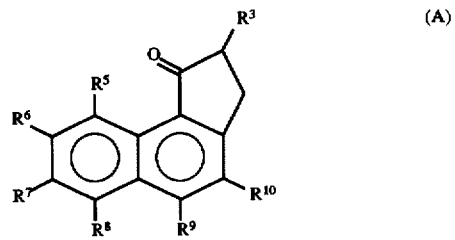

(A)

where $R^3$ and $R^5$ through $R^{10}$ are the same or different and are a hydrogen atom; a halogen atom (preferably a fluorine, chlorine or bromine atom); a hydrocarbyl group containing up to about 10 carbon atoms each (e.g., a $C_1$ to $C_{10}$, and preferably a $C_1$ to $C_4$ alkyl group, a $C_6$ to $C_{10}$ aryl group, a $C_3$ to $C_{10}$ cycloalkyl group, a $C_2$ to $C_{10}$, and preferably a $C_2$ to $C_4$ alkenyl group, a $C_7$ to $C_{10}$ aralkyl group, etc.); a halohydrocarbyl group containing up to about 10 carbon atoms and up to about 3 halogen atoms each; an —$NR_2$, —SR, —$OSiR_3$, —$SiR_3$, or —$PR_2$ group in which R is a halogen atom, preferably a chlorine atom, or a hydrocarbyl group containing up to about 10 carbon atoms. In preferred embodiments $R^3$ is an alkyl group, most preferably a methyl group, and at least four and most preferably all six of $R^5$ through $R^{10}$ are hydrogen atoms.

The 4,5-benzoindanols formed in this reaction likewise can exist in either of two isomeric forms derived from the isomeric forms of the 4,5-benzoindanone(s) used as the starting material. Such 4,5-benzoindanols are thus illustrated by formula (B) below which depicts the 4,5-benzoindan-1-ols. The 4,5-benzoindan-3-ols have the same formula except that the hydroxyl group is in the 3-position of the 5-membered ring instead of the 1-position as shown.

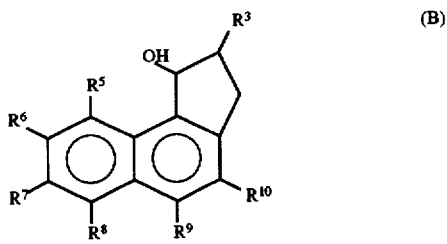

(B)

where $R^3$ and $R^5$ through $R^{10}$ are as described above.

Another embodiment of this invention is the process of forming 4,5-benzoindene which comprises reducing a 4,5-benzoindanone to a 4,5-benzoindanol as described above, and catalytically alehydrating the 4,5-benzoindanol (Formula (B) above) so formed. The 4,5-benzoindenes formed in this reaction can be depicted by the formula:

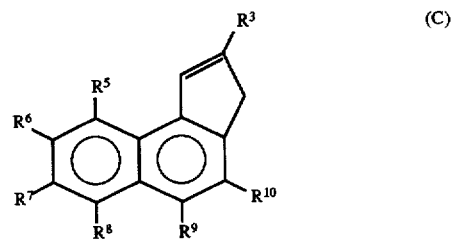

(C)

where $R^3$ and $R^5$ through $R^{10}$ are as described above. Formula (C) depicts an isomer having a double bond of the 5-membered ring in the 1-position. In another isomer that double bond can instead be in the 2-position, and mixtures of these respective isomers can be formed.

The preferred method of effecting the dehydration step involves use of an arylsulfonic acid catalyst such as p-toluenesulfonic acid. In conducting this reaction sequence the reduction of the benzoindanone (Formula (A) above) to the benzoindanol (Formula (B) above) is preferably terminated by quenching the reaction mixture with water or a suitable aqueous solution or mixture, and separating off the aqueous phase before proceeding with the catalytic dehydration reaction. By conducting the reduction step in a low boiling ether reaction medium such as tetrahydrofuran, the separations after the aqueous quench can be readily accomplished by extracting the quenched reaction mixture with a liquid hydrocarbon, preferably an aromatic hydrocarbon such as toluene or xylene, having a higher boiling point or nigher initial boiling point than the ether, and distilling at least the ether from the resultant extract. Use of an excess of the hydrocarbon provides, on completion of the distillation, a suitable predominately hydrocarbonaceous reaction medium in which to conduct the dehydration step. Moreover on completion of the dehydration, the water formed during the dehydration plus residual water, if any, from the quenching step, can be readily removed by azeotropic distillation. While the catalytic dehydration is best carried out using an arylsulfonic acid catalyst, other ways of performing the dehydration can be used especially for laboratory scale operations. Such methods include use of oxalic acid as dehydration catalyst or reaction of the benzoindanol with dehydrating substances such as magnesium sulfate or molecular sieves. For references describing such alternative albeit far less desirable procedures, see Rohrmann et al. at Column 9, lines 41–43.

In summary therefore, a preferred process sequence per this invention for converting a 4,5-benzoindanone to a 4,5-benzoindene comprises: (a) a 4,5-benzoindanone is reduced to a 4,5-benzoindanol in an ether-containing reaction medium by use of an alkali metal borohydride and water or an alcohol or a mixture thereof; (b) the reduction is terminated by quenching the reaction mixture with a suitably large mount of water (or appropriate aqueous mixture); (c) a separation is effected between the water and organic constituents of the reaction mixture, by extracting the quenched reaction mixture with a liquid hydrocarbon having a higher boiling point or nigher initial boiling point than the ether, and, if present, the alcohol; (d) distilling off said ether and, if present, the alcohol to leave a liquid hydrocarbon solution of the 4,5-benzoindanol; (e) catalytically dehydrating 4,5-benzoindanol so formed to the corresponding 4,5-benzoindene while in liquid hydrocarbon solution, and (f) removing water from the dehydration reaction mixture by azeotropic distillation. In this embodiment it is especially preferred that in Formulas (A), (B) and (C) above, $R^3$ be an alkyl group, most preferably a methyl group, and that at least four and most preferably all six of $R^5$ through $R^{10}$ be hydrogen atoms.

Another embodiment of this invention comprises converting the 4,5-benzoindenes (Formula C above) to a silicon-, germanium- or tin-bridged complex of the formula:

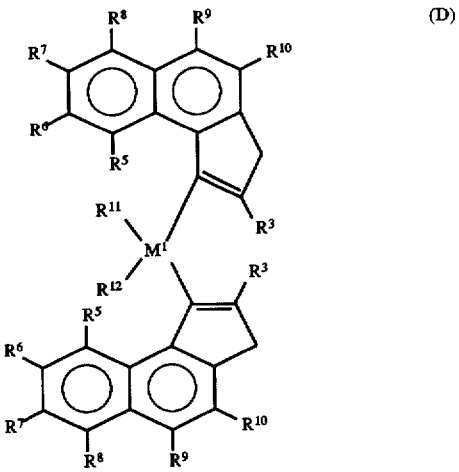

(D)

where $R^3$ and $R^5$ through $R^{10}$ are as described above, $M^1$ is a silicon, germanium or tin atom (preferably a silicon atom), and $R^{11}$ and $R^{12}$ are the same or different and are a hydrocarbyl group containing up to about 18 carbon atoms each (e.g., a $C_1$ to $C_{18}$, and preferably a $C_1$ to $C_4$ alkyl group, a $C_6$ to $C_{18}$ aryl group, a $C_3$ to $C_{18}$ cycloalkyl group, a $C_2$ to $C_{18}$, and preferably a $C_2$ to $C_4$ alkenyl group, a $C_7$ to $C_{18}$ aralkyl group, etc.); or a hydrocarbyl(oxyalkylene) or hydrocarbylpoly(oxyalkylene) group containing up to about 100 carbon atoms (preferably where the oxyalkylene moiety or moieties are oxyethylene and or oxymethylethylene, and in the case of long chain polyoxyalkylenes, the oxyalkylene moieties are in random or block arrangements. Most preferably, $M^1$ is a silicon atom; $R^{11}$ and $R^{12}$ are the same and are $C_1$ to $C_4$ alkyl groups, most preferably methyl or ethyl groups, $R^3$ is an alkyl group, most preferably a methyl group, and at least four and most preferably all six of $R^5$ through $R^{10}$ are hydrogen atoms.

To produce the compounds of Formula (D) above, the benzoindenes (Formula (C) above) are deprotonated with a strong base such as butyllithium and reacted with a suitable silicon, germanium or tin reactant, which can be depicted by the formula $R^{11}R^{12}M^1X_2$ where X is a halogen atom (preferably a chlorine or bromine atom) and $M^1$, $R^{11}$ and $R^{12}$ are as described above. In a particularly preferred embodiment of this invention these operations are conveniently conducted in a dialkyl ether medium, typically a lower alkyl ether such as diethyl ether, dipropyl ether, methyl tert-butyl ether, ethyl tert-butyl ether, methyl tert-amyl ether, or dibutyl ether, most preferably diethyl ether. Unlike the situation where tetrahydrofuran is used in this procedure, the use of a liquid dialkyl ether enables the bridged product to form a slurry which is easily separated from the liquid phase by such procedures as filtration, centrifugation or decantation. If a solvent such as tetrahydrofuran is used, it is likely that a oily product will be formed which is hard to handle and to separate cleanly without recourse to solvent exchanging and an excessive amount of washing. Thus use of a dialkyl ether such as diethyl ethyl has proven to greatly facilitate the separation and recovery of the bridged product, and accordingly makes this operation entirely feasible for use in large plant scale operations.

In still another embodiment, the bridged compound of Formula (D) above is transformed into a metallocene complex of the formula:

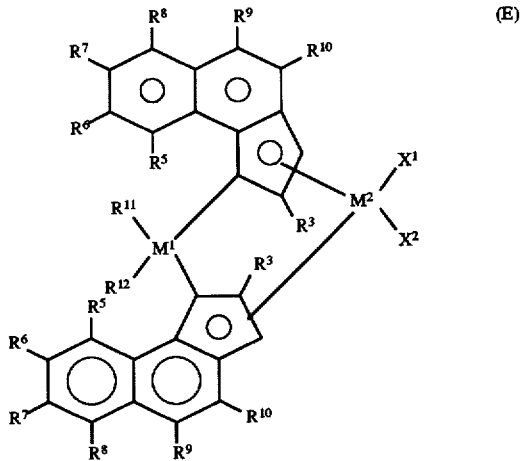

(E)

where $M^2$ is a group IV, V, or VI metal atom (i.e., Ti, Zr, Hf, V, Nb, Ta, Cr, Mo, or W); $X^1$ and $X^2$ are the same or different and each is a halogen atom (preferably a chlorine atom); and $M^1$, $R^3$ and $R^5$ through $R^{12}$ are as described above. Preferably $M^2$ is Ti, Zr or Hf, most preferably Zr; $X^1$ and $X^2$ are chlorine atoms; $M^1$ is a silicon atom; $R^{11}$ and $R^{12}$ are the same and are $C_1$ to $C_4$ alkyl groups, most preferably methyl or ethyl groups, $R^3$ is an alkyl group, most preferably a methyl group, and at least four and most preferably all six of $R^5$ through $R^{10}$ are hydrogen atoms.

Compounds of Formula (E) above are formed by deprotonating a bridged compound of Formula (D) above with a strong base such as butyllithium and reacting the deprotonated intermediate so formed with a suitable Group IV, V, or VI metal-containing reactant, such as a Group IV, V, or VI metal tetrahalide. The deprotonation is typically performed in a ether medium such as tetrahydrofuran or lower dialkyl ether. The metallation reaction is preferably conducted by adding the ether solution of the deprotonated intermediate portionwise to a preformed complex or mixture of the Group IV, V, or VI metal-containing reactant and an ether such as tetrahydrofuran in a hydrocarbon solvent such as toluene or xylenes or the like. However other solvent systems and modes of addition can be used.

Various compounds of Formula (E) are useful as components for catalyst systems for producing polyolefins such as polypropylene.

The following examples illustrate preferred procedures for conducting the various individual reactions and the overall sequence of steps that can be employed in the practice of this invention. It is to be clearly understood that these examples are for the purposes of illustrating current best modes for carrying out the operations. They are not intended to limit, and should not be construed as limiting, the invention to the specific procedures set forth therein.

EXAMPLE 1

Preparation of 2-Methyl-4,5-benzoindanone

A slurry of 577 g (4.322 mol) $AlCl_3$ in 250 mL of methylene chloride was cooled to 5° C. To the slurry 372 g (1.618 mol) of 2-bromoisobutyryl bromide was added over 0.75 hour. After stirring for 0.5 hour, a solution of 207 g (1.616 mol) of naphthalene in 500 mL, of methylene chloride was added at 5° C. over 1.5 hour. During the addition any HCl/HBr gas evolved overhead was scrubbed with a caustic solution. The resulting mixture was stirred for 0.5 hour at 5° C. and 1 hour at room temperature. The reaction slurry was then transferred to 2 to 3 liters of ice/water in a separate flask with agitation. HCl/HBr gas formed during the hydrolysis was scrubbed by a caustic solution. The organic phase (lower layer) of the hydrolyzed mixture was separated and saved. The upper aqueous layer was extracted once with 500 mL of methylene chloride. The combined organic phase and extract were washed with water (2×, 500 mL each) and the solvent was removed in vascuo to obtain crude product as a brown oil. The brown oil was flashed under 5 mm Hg vacuum and 158°–160° C. head temperature (or 170°–210° C. pot temperature) to collect 276 g (87% yield) of product as an orange oil. NMR analysis of the oil confumed it was 2-methyl-4,5-benzoindanone; GC analysis of the oil indicated it was 96% pure.

EXAMPLE 2

Preparation of 2-Methyl-4,5-benzoindanol and Conversion to 2-Methyl-4,5-benzoindene A solution of 2-methyl-4,5-benzoindanone (276 g, 1.408 mol) dissolved in 570 mL of THF and 570 mL of methanol was cooled to 5° C., and solid $NaBH_4$ (28 g, 0.74 mol) was added in portions to the solution over 45 minutes. After stirring for one hour at 5° C. and another hour at room temperature, the reaction mixture was quenched with 570 mL of water and followed by 60 mL of concentrated HCl (to bring the pH of the mixture to 2). The alcohols (2-methyl-4,5-benzoindanols) formed were extracted with toluene (2×, 500 mL each) and the combined extracts were washed with water (2×, 300 mL). The THF/methanol solvent in the toluene extract was distilled off under atmospheric pressure. When the pot temperature reached ~113° C., the distillation was stopped and the mixture was cooled. Once the pot temperature was cooled down to about 80° C., 0.15 g of p-toluenesulfonic acid monohydrate was added, and the mixture was heated up again for one more hour to azeotrope off water (25 mL theory). After the azeotropic distillation was completed, all the toluene solvent in the mixture was removed under vacuum. 2-Methyl-4,5-benzoindene (254 g, 100% yield) was obtained as a brown oil. Analysis by NMR and GC confirmed the structure of the product and its purity was more than 95%.

EXAMPLE 3

Preparation of Dimethylsilylbis(2-methyl-4,5-benzoindene)

A solution of 567 mL (1.423 mol) of BuLi solution (2.5 M in hexanes) was added at room temperature over 1.5 hour to a solution of 256 g (1.422 mol) of 2-methyl-4,5-benzoindene in one liter of dry diethyl ether. The mixture was allowed to reflux (39°–43° C.) during the addition. After the addition, the mixture was heated at reflux for one hour and then cooled. At room temperature, 92 g (0.7132 mol) of dichlorodimethylsilane was added to the pot over a period of 1.5 hours. The resulting mixture was stirred at room temperature overnight to form a slurry. Next morning 400 mL of ether was distilled off from the mixture and the slurry in the pot was cooled to 10° C. The precipitated dimethylsilylbis (2-methyl-4,5-benzoindene) and LiCl solids were filtered, and the cake was successively washed with ether (2×, 100 mL each), aqueous methanol (2×, 100 mL methanol+100 mL water, each) and followed by acetone (2×, 50 mL each). The cake was dried under 5 mm Hg/50° C. to thoroughly remove all methanol/water to give 178 g (60 % yield) of dimethylsilylbis(2-methyl-4,5-benzoindene) as tan-colored solids. The structure and purity of this product were confirmed by NMR analysis.

EXAMPLE 4

Preparation of Dimethylsilylbis-(2-methyl-4,5-benzoindenyl)zirconium Dichloride

Dimethylsilylbis(2-methyl-4,5-benzoindene) (100.27 g, 0.241 mol) was partially dissolved in 300 mL of THF. This slurry was cooled to 0° C. and then two equivalents of n-BuLi (193 mL of 2.5M in hexanes; 0.48 mol) were added dropwise. A clear, amber solution of the dilithium derivative of the silyl-bridged reactant formed. After the addition was complete, the reaction mixture was allowed to warm to room temperature.

In a second flask, ZrCl$_4$ (56.8 g; 0.244 mol) was slurred in 500 mL of anhydrous toluene. THF (70 g; 0.97 mol) was added to this slurry to form the complex, ZrCl$_4$(THF)$_2$. The reaction was stirred overnight and then the solution of the dilithium derivative was added dropwise to the ZrCl$_4$(THF)$_2$ slurry over 75 minutes. An orange=yellow slurry formed. After 2 hours, the reaction mixture was heated in an oil bath and 350 mL of solvent were flash distilled. A vacuum was applied and an additional 450 mL of volatiles were removed. The slurry was stirred for 3 hours and then the solids were isolated by filtration on a coarse frit. The solids were washed with 20 mL of toluene, 40 mL of hexanes and then dried in vacuo. The yield of yellow solid was 100.3 grams. A $^1$H NMR showed the metallocene was present in a rac/meso ratio of 1:1.

The crude product was slurried in 900 mL of anhydrous THF and heated to reflux overnight. The slurry was cooled to room temperature and filtered on a coarse frit. The yellow solids were washed with 35 mL of THF and dried in vacuo. The dried weight of dimethhylsilylbis(2-methyl-4,5-benzoindenyl)zirconium dichloride was 41.4 grams (30 % yield based on the initial silyl-bridged reactant). $^1$H NMR determined the rac/meso ratio to be greater than 99:1.

The above purification procedure for the crude product is highly effective. Typically the slurry is formed in a liquid aprotic, polar solvent (e.g., ethers, ketones, tertiary amines, etc.) and held at a temperature in the range of about 40° to about 120° C. for about 3 to about 12 hours. Agitation is helpful. Use of refluxing tetrahydrofuran is particularly useful.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that the substance, component or ingredient may have lost its original identity through a chemical reaction or transformation during the course of such contacting, blending or mixing operations is thus wholly immaterial for an accurate understanding and appreciation of this disclosure and the claims thereof.

Each and every patent or other publication referred to in any portion of this specification is incorporated in toto into this disclosure by reference for all purposes, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises:
   1) mixing together at least one of each of the following: (a) a 4,5-benzoindanone, (b) an alkali or alkaline earth metal borohydride or alkali or alkaline earth metal aluminum hydride, (c) a hydroxyl-containing compound capable of interacting with (b) to serve as a hydrogen source, and (d) at least one ether;
   2) maintaining the resultant mixture under reaction conditions causing a 4,5-benzoindanol to be formed;
   3) terminating the reaction by quenching the reaction mixture with water or an aqueous mixture; and
   4) separating 4,5-bertzoindanol from ether and water by extracting the quenched reaction mixture with a liquid aromatic hydrocarbon having a higher boiling point or a higher initial boiling point than the ether, and distilling the resultant extract to leave a liquid hydrocarbon solution of the 4,5-benzoindanol.

2. A process according to claim 1 wherein the ether comprises at least one cyclic ether.

3. A process according to claim 1 wherein the ether is tetrahydrofuran.

4. A process according to claim 1 wherein the 4,5-benzoindanone is a 2-hydrocarbyl-4,5-benzoindanone.

5. A process according to claim 4 wherein the 2-hydrocarbyl-4,5-benzoindanone is a major mount of 2-methyl-4,5-benzoindan-1-one and a minor amount of 2-methyl-4,5-benzoindan-3-one.

6. A process according to claim 1 wherein (b) is at least one compound of the formula $AMH_x(OR)_y$ wherein A is an alkali metal, M is boron or aluminum, R is hydrocarbyl, x is an integer in the range of 2 to 4, and y is an integer in the range of 0 to 2, the sum of x and y being 4.

7. A process according to claim 1 wherein (b) is sodium borohydride and (c) is water or an alcohol.

8. A process according to claim 1 wherein (b) is an alkali metal aluminum tetrahydride and (c) is water or an alcohol.

9. A process according to claim 1 wherein the 4,5-benzoindanone is a 2-alkyl-4,5-benzoindanone, wherein (b) is an alkali metal borohydride and wherein (c) is water or an alcohol.

10. A process according to claim 9 wherein the ether is at least predominately tetrahydrofuran, wherein the 2-alkyl-4,5-benzoindanone is a major amount of 2-methyl-4,5-benzoindan-1-one and a minor amount of 2-methyl-4,5-benzoindan-3-one, and wherein (b) is sodium borohydride.

11. A process which comprises:
1) mixing together at least one of each of the following:
   (a) a 4,5-benzoindanone, (b) an alkali or alkaline earth metal borohydride or alkali or alkaline earth metal aluminum hydride, (c) a hydroxyl-containing compound capable of interacting with (b) to serve as a hydrogen source, and (d) at least one ether;
2) maintaining the resultant mixture under reaction conditions causing a 4,5-benzoindanol to be formed;
3) terminating the reaction by quenching the reaction mixture with water or an aqueous mixture;
4) extracting the quenched reaction mixture with a liquid hydrocarbon having a higher boiling point or a higher initial boiling point than the ether;
5) distilling the resultant extract to leave a liquid hydrocarbon solution of the 4,5-benzoindanol; and
6) catalytically dehydrating said 4,5-benzoindanol using an arylsulfonic acid catalyst to thereby form a 4,5-benzoindene.

12. A process according to claim 11 wherein the 4,5-benzoindanone is a 2-alkyl-4,5-benzoindanoine, wherein (b) is an alkali metal borohydride and wherein (c) is water or an alcohol.

13. A process according to claim 12 wherein the ether is at least predominately tetrahydrofuran, wherein the 2-alkyl-4,5-benzoindanone is a major mount of 2-methyl-4,5-benzoindan-1-one and a minor amount of 2-methyl-4,5-benzoindan-3-one, and wherein (b) is sodium borohydride.

14. A process according to claim 11 wherein the 4,5-benzoindanone is a 2-alkyl-4,5-benzoindanone, wherein (b) is an alkali metal borohydride, wherein (c) is water or an alcohol, wherein the liquid hydrocarbon has a higher boiling point or a higher initial boiling point not only than the ether, but, if present, the alcohol as well, wherein not only said ether but, if present, said alcohol are distilled off to leave a liquid hydrocarbon solution of the 4,5-benzoindanol, and wherein the catalytic dehydration is conducted without isolating the 4,5-benzoindanol from the liquid hydrocarbon solution.

15. A process according to claim 14 wherein the ether is at least predominately tetrahydrofuran, wherein the 2-alkyl-4,5-benzoindanone is a major amount of 2-methyl-4,5-benzoindan-1-one and a minor amount of 2-methyl-4,5-benzoindan-3-one, and wherein (b) is sodium borohydride.

16. A process according to claim 15 wherein (c) is an alcohol and wherein the liquid hydrocarbon is at least one aromatic hydrocarbon capable of forming an azeotrope with water.

17. A process according to claim 16 wherein the alcohol is methanol and wherein the liquid hydrocarbon consists essentially of toluene.

18. A process which comprises:
1) mixing together at least one of each of the following:
   (a) a 4,5-benzoindanone, (b) an alkali or alkaline earth metal borohydride or alkali or alkaline earth metal aluminum hydride, (c) a hydroxyl-containing compound capable of interacting with (b) to serve as a hydrogen source, and (d) at least one ether;
2) maintaining the resultant mixture under reaction conditions causing a 4,5-benzoindanol to be formed;
3) terminating the reaction by quenching the reaction mixture with water or an aqueous mixture;
4) extracting the quenched reaction mixture with a liquid hydrocarbon having a higher boiling point or a higher initial boiling point than the ether;
5) distilling the resultant extract to leave a liquid hydrocarbon solution of the 4,5-benzoindanol;
6) catalytically dehydrating said 4,5-benzoindanol using an arylsulfonic acid catalyst to thereby form a 4,5-benzoindene; and
7) deprotonating said 4,5-benzoindene with a strong base and reacting the resultant deprotonated intermediate with a reactant which in its original condition can be depicted by the formula $R^{11}R^{12}M^1X_2$ where $R^{11}$ and $R^{12}$ are the same or different and each is (i) a hydrocarbyl group containing up to about 18 carbon atoms or (ii) a hydrocarbyl(oxyalkylene) or hydrocarbylpoly (oxyalkylene) group containing up to about 100 carbon atoms; $M^1$ is a silicon, germanium or tin atom; and X is a halogen atom; such that a silicon-, germanium- or tin-bridged complex of the 4,5-benzoindene is formed.

19. A process according to claim 18 wherein $R^{11}$ and $R^{12}$ are the same and are $C_1$ to $C_4$ alkyl groups, wherein $M^1$ is a silicon atom, and wherein X is a bromine or chlorine atom.

20. A process according to claim 19 wherein the 4,5-benzoindanone is a 2-alkyl-4,5-benzoindanone, wherein (b) is an alkali metal borohydride and wherein (c) is water or an alcohol.

21. A process according to claim 20 wherein the ether is at least predominately tetrahydrofuran, wherein the 2-alkyl-4,5-benzoindanone is a major mount of 2-methyl-4,5-benzoindan-1-one and a minor amount of 2-methyl-4,5-benzoindan-3-one, and wherein (b) is sodium borohydride.

22. A process according to claim 19 wherein the 4,5-benzoindanone is a 2-alkyl-4,5-benzoindanone, wherein (b) is an alkali metal borohydride, wherein (c) is water or an alcohol, wherein the liquid hydrocarbon has a higher boiling point or a higher initial boiling point not only than the ether, but, if present, the alcohol as well, wherein not only said ether but, if present, said alcohol are distilled off to leave a liquid hydrocarbon solution of the 4,5-benzoindanol, and wherein the catalytic dehydration is conducted without isolating the 4,5-benzoindanol from the liquid hydrocarbon solution.

23. A process according to claim 22 wherein the ether is at least predominately tetrahydrofuran, wherein the 2-alkyl-4,5-benzoindanone is a major amount of 2-methyl-4,5-benzoindan-1-one and a minor amount of 2-methyl-4,5-benzoindan-3-one, and wherein (b) is sodium borohydride.

24. A process according to claim 23 wherein (c) is an alcohol and wherein the liquid hydrocarbon is predominately one or more one aromatic hydrocarbons capable of forming azeotrope with water.

25. A process according to claim 18 wherein the strong base is a lithium alkyl.

26. A process which comprises:
1) mixing together at least one of each of the following: (a) a 4,5-benzoindanone, (b) an alkali or alkaline earth metal borohydride or alkali or alkaline earth metal aluminum hydride, (c) a hydroxyl-containing compound capable of interacting with (b) to serve as a hydrogen source, and (d) at least one ether;
2) maintaining the resultant mixture under reaction conditions causing a 4,5-benzoindanol to be formed;
3) terminating the reaction by quenching the reaction mixture with water or an aqueous mixture;
4) extracting the quenched reaction mixture with a liquid hydrocarbon having a higher boiling point or a higher initial boiling point than the ether;
5) distilling the resultant extract to leave a liquid hydrocarbon solution of the 4,5-benzoindanol;
6) catalytically dehydrating said 4,5-benzoindanol using an arylsulfonic acid catalyst to thereby form a 4,5-benzoindene;
7) deprotonating said 4,5-benzoindene with a strong base and reacting the resultant deprotonated intermediate with a reactant which in its original condition can be depicted by the formula $R^{11}R^{12}M^1X_2$ where $R^{11}$ and $R^{12}$ are the same or different and each is (i) a hydrocarbyl group containing up to about 18 carbon atoms or (ii) a hydrocarbyl(oxyalkylene) or hydrocarbylpoly(oxyalkylene) group containing up to about 100 carbon atoms; $M^1$ is a silicon, germanium or tin atom; and X is a halogen atom; such that a silicon-, germanium- or tin-bridged complex of the 4,5-benzoindene is formed; and
8) deprotonating said bridged complex with a strong base and reacting the resultant deprotonated intermediate with a Group IV, V, or VI metal tetrahalide to thereby form a silicon-, germanium- or tin-bridged Group IV, V, or VI metal-containing metallocene complex.

27. A process according to claim 26 wherein $R^{11}$ and $R^{12}$ are the same and are $C_1$ to $C_4$ alkyl groups, wherein $M^1$ is a silicon atom, wherein X is a bromine or chlorine atom, and wherein the Group IV, V, or VI metal-containing reactant is a zirconium tetrahalide.

28. A process according to claim 27 wherein the 4,5-benzoindanone is a 2-alkyl-4,5-benzoindanone, wherein (b) is an alkali metal borohydride, wherein (c) is water or an alcohol, and wherein the zirconium tetrahalide is zirconium tetrachloride or zirconium tetrabromide.

29. A process according to claim 28 wherein the ether is at least predominately tetrahydrofuran, wherein the 2-alkyl-4,5-benzoindanone is a major mount of 2-methyl-4,5-benzoindan-1-one and a minor amount of 2-methyl-4,5-benzoindan-3-one, and wherein (b) is sodium borohydride.

30. A process according to claim 27 wherein the liquid hydrocarbon is a liquid aromatic hydrocarbon.

31. A process according to claim 27 wherein the 4,5-benzoindanone is a 2-alkyl-4,5-benzoindanone, wherein (b) is an alkali metal borohydride, wherein (c) is water or an alcohol, wherein the liquid hydrocarbon has a higher boiling point or a higher initial boiling point not only than the ether, but also, if present, the alcohol, wherein said ether and, if present, said alcohol are distilled off, and wherein the catalytic dehydration is conducted without isolating the 4,5-benzoindanol from the liquid hydrocarbon solution.

32. A process according to claim 31 wherein the ether is at least predominately tetrahydrofuran, wherein the 2-alkyl-4,5-benzoindanone is a mixture of a major mount of 2-methyl-4,5-benzoindan-1-one and a minor mount of 2-methyl-4,5-benzoindan-3-one, and wherein (b) is sodium borohydride.

33. A process according to claim 32 wherein (c) is an alcohol and wherein the liquid hydrocarbon consists essentially of at least one aromatic hydrocarbon capable of forming an azeotrope with water.

34. A process according to claim 26 wherein each of the respective strong bases used in 7) and in 8) is a lithium alkyl.

35. A process according to claim 26 wherein the deprotonating of the 4,5-benzoindene with a strong base and the reacting of the resultant deprotonated intermediate are conducted while the 4,5-benzoindene and the resultant deprotonated intermediate, respectively, are dissolved in a liquid lower dialkyl ether.

36. A process according to claim 35 wherein the 4,5-benzoindene is a 2-alkyl-4,5-benzoindene, wherein each of the respective strong bases used in 7) and in 8) is a lithium alkyl, and wherein said reactant is a dialkyldihalosilane.

37. A process according to claim 36 wherein the alkyl groups of the dialkyldihalosilane contain no more than 4 carbon atoms each.

38. A process according to claim 35 wherein the 4,5-benzoindene is 2-methyl-4,5-benzoindene, wherein each of the respective strong bases used in 7) and in 8) is butyllithium, wherein said ether is diethyl ether, wherein said reactant is dichlorodimethylsilane, and wherein said solids are separated from the liquid phase by filtration.

39. A process which comprises:
1) mixing together at least one of each of the following: (a) a 4,5-benzoindanone, (b) an alkali or alkaline earth metal borohydride or alkali or alkaline earth metal aluminum hydride, and (c) a hydroxyl-containing compound selected from the group consisting of water, an alcohol, and a mixture thereof capable of interacting with (b) to serve as a hydrogen source, under reaction conditions causing a 4,5-benzoindanol to be formed;
2) terminating the reaction by quenching the reaction mixture with water or an aqueous mixture;
3) extracting the quenched reaction mixture with a liquid hydrocarbon;
4) distilling the resultant extract to leave a liquid hydrocarbon solution of the 4,5- benzoindanol;
5) catalytically dehydrating said 4,5-benzoindanol using a arylsulfonic acid catalyst to thereby form a 4,5-benzoindene;
6) deprotonating said 4,5-benzoindene with a strong base and reacting the resultant deprotonated intermediate with a reactant which in its original condition can be depicted by the formula $R^{11}R^{12}M^1X_2$ where $R^{11}$ and $R^{12}$ are the same or different and each is (i) a hydrocarbyl group containing up to about 18 carbon atoms or (ii) a hydrocarbyl(oxyalkylene) or hydrocarbylpoly(oxyalkylene) group containing up to about 100 carbon atoms; $M^1$ is a silicon, germanium or tin atom; and X is a halogen atom; such that a silicon-, germanium- or tin-bridged complex of the 4,5-benzoindene is formed;

7) deprotonating said bridged complex with a strong base and reacting the resultant deprotonated intermediate with a Group IV, V, or VI metal tetrahalide to thereby form solids comprising a silicon-, germanium- or tin-bridged Group IV, V, or VI metal-containing metallocene complex; and 8) forming and heating a slurry of said solids at an elevated temperature in an aprotic, polar solvent so as to extract impurities from said solids to said solvent and then separating the impurity-containing solvent and the solids from each other.

40. A process according to claim 39 wherein said aprotic, polar solvent is an ether.

41. A process in accordance to claim 40 wherein said ether is tetrahydrofuran.

* * * * *